United States Patent [19]

Atkinson et al.

[11] Patent Number: 4,669,453
[45] Date of Patent: Jun. 2, 1987

[54] LAVAGE SYSTEM

[75] Inventors: Robert W. Atkinson, Dover; Michael J. Laco, Sherrodsville, both of Ohio

[73] Assignee: Snyder Laboratories, Inc., Dover, Ohio

[21] Appl. No.: 445,796

[22] Filed: Dec. 1, 1982

[51] Int. Cl.$^4$ ............................................. A61H 9/00
[52] U.S. Cl. ....................................... 128/66; 433/80
[58] Field of Search .................. 128/66; 239/102; 604/30; 433/80,

[56] References Cited

U.S. PATENT DOCUMENTS

| | | | |
|---|---|---|---|
| 2,087,654 | 7/1937 | Pieper | 433/80 |
| 4,416,628 | 11/1983 | Cammack | 433/80 |

FOREIGN PATENT DOCUMENTS

| | | | |
|---|---|---|---|
| 2322191 | 5/1973 | Fed. Rep. of Germany | 433/80 |
| 2433819 | 11/1974 | Fed. Rep. of Germany | 433/80 |
| 2920009 | 5/1979 | Fed. Rep. of Germany | 433/80 |

*Primary Examiner*—Gene Mancene
*Assistant Examiner*—Wenceslao J. Contreras
*Attorney, Agent, or Firm*—Paul David Schoenle

[57] ABSTRACT

A mechanism, such as a motor driving a pump, creates a pulsating fluid flow. A sensor senses an operating condition of the system and provides a signal representative of the condition. A controller responsive to the signal controls the pulsating fluid flow mechanism in a predetermined manner in accordance with the condition sensed. In one aspect the sensor is a pressure transducer which senses when a throttle valve on a lavage head shuts off or turns on the fluid flow and provides a signal to a controller which shuts off or turns on the motor. In another aspect the sensor is a thermistor which senses the temperature of the motor and provides a signal for controlling the power input to the motor to compensate for the effect of temperature on the performance of the motor.

2 Claims, 12 Drawing Figures

LAVAGE SYSTEM

BACKGROUND OF THE INVENTION

1. Field of the Invention

The invention in general relate to the field of medical or therapeutic lavage, and more particularly to a mechanized lavage system in which the rate of fluid flow and the average fluid pressure are variable.

2. Description of the Prior Art

Lavage, or the washing of tissue, is perhaps as old as medicine itself. In the early years it consisted of the application of fluid, generally a liquid such as water, to tissue to wash away dirt or debris. In more modern times it has become more important, and more thorough, due to an awareness of bacteria and other organisms that may cause infection. In the last several decades, mechanized lavage systems have become common, however many surgeons and other physicians have preferred to use syringes or other hand-operated means for lavage because prior art mechanized systems have not been suitable for delicate and critical cleansing tasks.

Before proceeding to the discussion of prior art mechanized devices it will be useful to clarify terminology. The word "lavage" is used ambiguously in the literature, sometimes referring to a pulsating stream type washing or therapy, sometimes referring to a stream type of washing, and sometimes also including an aspiration function. In this document, unless the context clearly indicates otherwise, "irrigation" shall mean the stream type of washing, "pulsatile lavage" shall mean the pulsating type of washing or therapy, and the word "lavage" shall mean the broadest sense of the term, referring to any one of, or combinations of irrigation, pulsatile lavage, and aspiration. Further, in this document the term "operating condition" condition refers to a thermodynamic variable of the system or a portion of the system, such as pressure, volume, temperature, and pulsation frequency, and any variable directly dependent on these, such as the rate of fluid flow (which depends directly on pressure and volume), or the internal resistance of electric driving motor coils (which depends directly on temperature).

Typical prior art lavage systems are described in U.S. Pat. Nos. 3,912,168 issued to Keith M. Mullins, et al. and 3,993.054 issued to Gordon Arthur Newman. In these systems the frequency of pulsation is generally not variable and the pressure and rate of flow of fluid through the system is controllable only through crude throttle type controls. Such controls are difficult to operate and are prone to producing a sudden unwanted burst of pulsatile flow and/or suction when it was not desired. This needs to happen only once during a critical surgical or other medical operation and the surgeons will return to their more familiar hand operated systems.

U S. Pat. No. 4,299,221 discusses the control problems with the prior art, and attempts to overcome them by using a mechanized valve in the lavage head which is powered by air pressure. In doing so, the device lost to a significant degree the desirable features of simplicity and inexpensive construction which permitted the prior devices to be disposable, which is preferable in devices whose puspose is cleansing open wounds, and also greatly increased the problems of resterilization, which is absolutely necessary in such devices if they are not disposable.

The prior art systems tend toward nonreproducibility of results. That is, different pulsation frequencies and different maximum pressures and rates of flow would be produced by the system depending upon whether it had just been turned on, whether it had been operating for some time, and whether the throttle controls had been closed down and the instrument laid aside while the physician attended to another procedure. For example, a physician might be accustomed to one flow from the system, then turn it off for a moment and find that when he picked it back up again the system provided a somewhat different flow. Similiarily, the flow might change during the course of use, even though the physician did not vary his use of the hand controls.

SUMMARY OF THE INVENTION

By providing a system in which the operating conditions assist the surgeon in the control of the device, rather than fight the surgeon, the present invention has overcome the control problems in a manner that is much more satisfactory than that provided in the prior art, for example U.S. Pat. No. 4,299,221. Surprisingly, the better results have been achieved in a device that appears, from the point of view of the surgeon and with regard to the features of disposability and sterilizability, to be simpler than the prior art devices that attempted to solve these problems.

The invention provides a lavage system comprising a means for producing a pulsatile fluid flow, a means for sensing an operating condition of the system and for providing a signal representative of the condition, and a means responsive to the signal for controlling the means for producing the pulsatile flow in a predetermined manner in accordance with the condition sensed. In one aspect of the invention the operating condition is the temperature of at least a portion of the system and the means for sensing is a means for sensing the temperature. In this aspect, the portion of the system the temperature of which is sensed is preferably the motor, which in the preferred embodiment is an electric motor; there is a means for furnishing a power signal to the motor, and the means for controlling comprises a means for changing the power signal in a manner that compensates for the effect of the change in temperature on the performance of the motor. In another aspect, the operating condition is the fluid pressure within at least a portion of the system, and the means for sensing is a means for sensing the pressure. In this aspect there is preferably a lavage head including a fluid outlet, a fluid conduit connecting the means for producing a pulsatile fluid flow and the lavage head, and a means on the lavage head for changing the fluid flow at the outlet, thereby changing pressure in the system. In this aspect the means for controlling preferably is a means for turning the means for producing a fluid flow off when the pressure exceeds a predetermined value and for turning the means for producing a fluid flow on when the pressure equals or falls below that value. In this manner, the means for changing the fluid flow at the lavage head, which preferably is a throttle valve, effectively controls the means for producing a pulsatile fluid flow. In a third aspect of the invention the operating condition is the rate of flow of fluid in at least a portion of the system, and the means for sensing is a means for sensing the rate of fluid flow.

These control mechanisms appear to have eliminated most if not all of the erratic behavior in prior art systems, and thus it is believed that the system of the invention will lead to much more acceptance of the mechanized lavage system among physicians, especially in situations in which the delicacy of control and reproducibility of performance are desirable. At the same time the lavage system according to the invention has been found to be much more efficient than previous systems, and has a substantially lower noise level, thus making it very welcome in the hospital environment.

Numerous other aspects, features, objects and advantages of the invention will now become apparent from the following detailed description when read in conjunction with the accompanying drawings, in which:

DESCRIPTION OF THE PREFERRED EMBODIMENT

Figure 1:
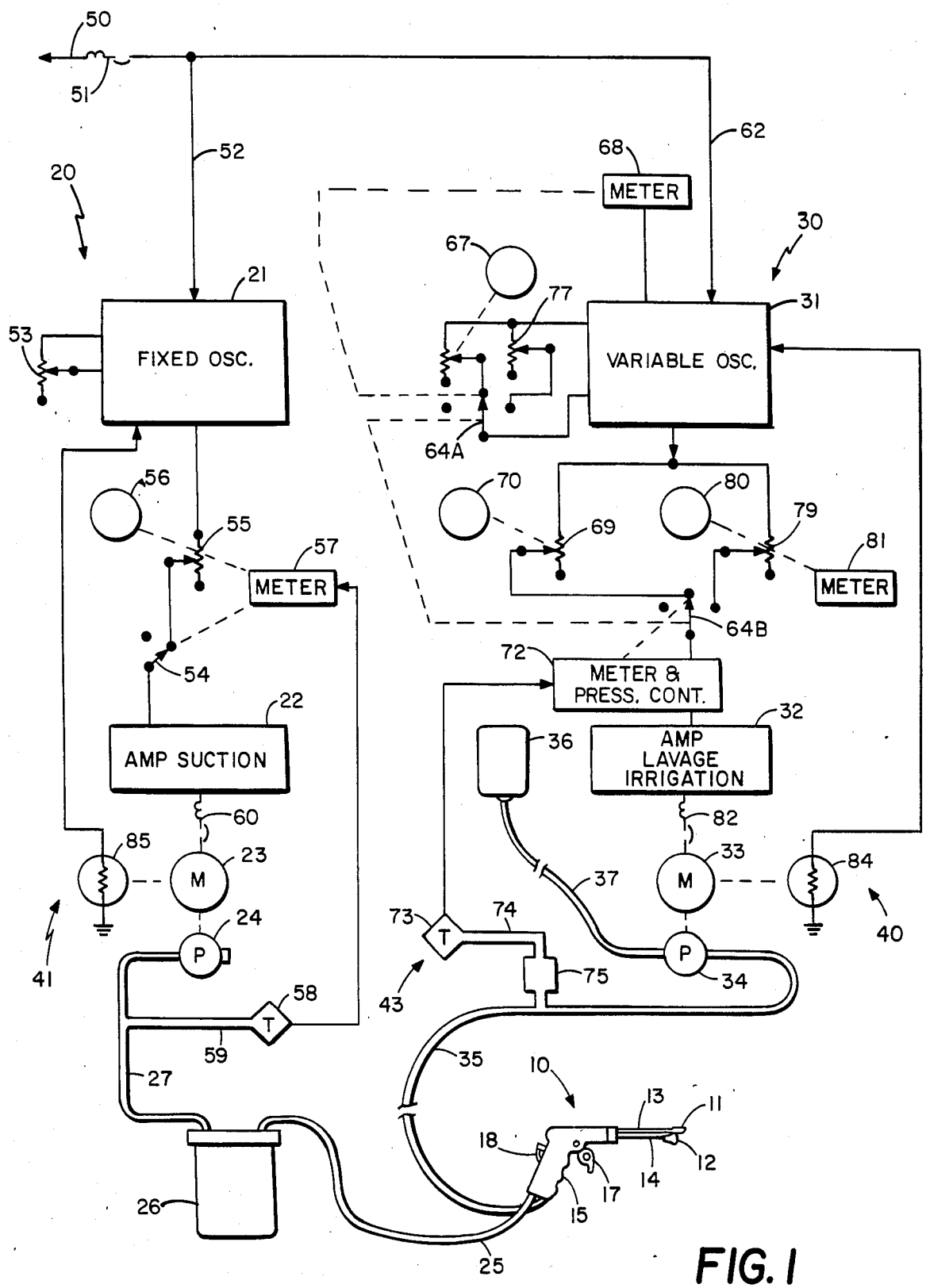
FIG. 1 is a diagrammatic illustration of the invention showing the various functional elements making up the invention in the preferred embodiment.

Referring to FIG. 1, a lavage system, according to the preferred embodiment of the invention is shown. A lavage head 10 having suction nozzle 11 and a pulsatile lavage/irrigation nozzle 12 it is connected via tube 25 to a means 20 for providing suction and via tube 35 to a means 30 for providing a pulsatile lavage and/ or irrigation fluid flow. The means 20 for providing suction generally comprises a fixed oscillator 21, a suction amp 22, a suction motor 23, and a suction pump 24. The means 30 for providing the pulsatile lavage/irrigation flow generally comprises a variable oscillator 31, a lavage/irrigation amp 32, a lavage/irrigation motor 33 and a lavage/irrigation pump 34. Temperature sensing and control means 40 and 41 and pressure sensing and control means 43, which shall be described in more detail shortly, each provide a means for sensing an operating condition of the system and for controlling means 20 and 21 in a predetermined manner.

Having provided a brief orientation to the drawings and the functions of the preferred system we shall now proceed with a more detailed description.

Lavage handpiece 10 includes a suction nozzle 11 which communicates with line 25 through tube 13 and a pulsatile lavage/ irrigation nozzle 12 which communicates with line 35 through tube 14, and a handpiece body 15. The handpiece body 15 has two interior passageways (not shown) through which tubes 25 and 35 pass to connect to the ends of tubes 14 and 13 respectively. Handpiece body 15 also includes pinch valve 70 for controlling the flow of pulsatile lavage/irrigation fluid and pinch valve 18 for controlling the suction flow. Valves 17 and 18 are throttle valves of a simple but effective design that is more fully discussed in a companion application to the present one, but for purposes of the present invention they may take on a variety of well known conventional forms, and thus they will not be discussed in detail herein. An inverted container of a fluid such as sterile saline solution is connected to pump 34 via line 37 to provide a source of pulsatile lavage/irrigation fluid. The end of line 25 opposite handpiece 10 is connected to drainage tank 26, which tank is in turn connected to pump 24 via line 27.

Turning now to the means for producing the suction and pulsatile lavage/irrigation fluid flows, electrical power is provided to the system through electrical line 50 through circuit breaker 51. Power line 52 applies power to fixed oscillator 21. Fixed oscillator 21 is only "fixed" in the sense that no front panel control is provided for its oscillation frequency, which determines the oscillation frequency of the suction motor 23. The oscillation frequency of fixed oscillator 21 is determined by variable resistance 53 which is set by a "back panel" control. Switch 54 is the "on" "off" suction switch. The vertical position of switch 54 in the drawing is the open circuit or "off" position. When turned to its right position switch 54 connects fixed oscillator 21 with the suction amplifier 22 through variable resistance 55. Variable resistance 55 is controlled by knob 56 which is a front panel control of the lavage system, which determines the amplitude of the input signal to suction amp 22 and thus the power applied to motor 23. In the right position switch 54 also turns on meter 57 which is connected to and displays the output of suction transducer 58, which in turn is connected to suction line 27 via line 59. The output of suction amplifier 22 is applied to motor 23 through circuit breaker 60. Motor 23 is mechanically connected to pump 24 to drive the pump.

Power is applied to variable oscillator 31 via electrical line 62. Switches 64A and 64B are the two poles of a double pole triple throw front panel switch 64 (not shown in FIG. 1) which controls the pulsatile lavage and irrigation function. Switches 64A and 64B thus move in unison. The far left position of switches 64A and 64B is an open circuit "off" position. The vertical position is the pulsatile lavage or "lavage" mode. In the vertical position switch 64A connects variable resistance 66 into the variable oscillator 31 circuit. Variable resistance 66 is controlled by front panel knob 67 to allow the user to set the oscillation frequency of variable oscillator 31 and thus motor 33. In the vertical position switch 64A also turns on meter 68 to read the oscillation frequency of variable oscillator 31. In the vertical position switch 64B connects variable oscillator 31 to the lavage/irrigation amplifier 32 (here "lavage" is short for pulsatile lavage) through variable resistance 69. Variable resistance 69 is controlled by front panel knob 72 to allow the user to set the size of the variable oscillator signal fed into amp 32 and thus determine the power applied to motor 33. In the vertical position switch 64B also turns meter 72 on. Meter 72 receives and displays the output signal from pressure transducer 70 in pounds per square inch (P.S.I.). Pressure transducer 73 is connected to line 35 via line 74 and filter 75. Filter 75 prevents microorganisms from passing from transducer 73 to line 35 and thus prevents transducer 73 from contaminating the sterile fluid in line 35. In the far left position, switch 64A connects variable resistance 77 into the circuit of variable oscillator 31. Variable resistance 77 is set by a back panel adjustment to "fix" the oscillation frequency of variable oscillator 31. With switch 64A in this position there is no front panel adjustment to the variable oscillator frequency, which mode is called the irrigation mode. At the same time that switch 64A is moved to the far right position switch 64B moves to the far right position, in which position it connects variable oscillator 31 to the lavage/irrigation amplifier 32 via variable resistance 79. Variable resistance 79 is controlled by the front panel knob 80 to provide the power adjustment to motor 33 in the irrigation mode. In the far right position switch 64B also activates meter 81 to read the output of variable resistance 79, which is a measure of the power applied to amp 32. The meter 81 is calibrated in percent of flow in the embodiment disclosed. In both the lavage and irrigation modes, power is applied from amp 32 to motor 33 through circuit breaker 82.

From the above it can be seen that the preferred system can be controlled in three "on" modes; "lavage", "irrigation", and "suction". Further, "lavage" when used in connection with knob 64 (64A and 64B) is short for the term pulsatile lavage used elsewhere herein. Moreover, both the "lavage" and "irrigation" modes provide irrigation in a sense that they both provide a stream of liquid. Likewise, while in the present embodiment the "lavage" mode does not control suction, suction is generally considered to be an integral part of surgical lavage. For this reason, the choice of terminology chosen to distinguish the three functions of the preferred system should not be considered to be limiting when these terms are used in somewhat different senses in other contexts.

Turning now to the primary subject of the present invention, a means for sensing an operating condition of the system and providing a signal representative of that condition is provided by a temperature sensing and control system shown generally at 40, a pressure sensing and control system shown generally at 43, and another temperature sensing and control system shown generally at 41. In the preferred embodiment system 40 comprises a thermistor 84 mounted on motor 33, variable oscillator 31, and amplifier 32. System 41 comprises a thermistor 85 mounted on motor 23, fixed oscillator 21, and amplifier 22. Circuits 40 and 41 are identical in function and construction, therefore the discussions shall be primarily limited to the discussion of circuit 40.

Figure 2:
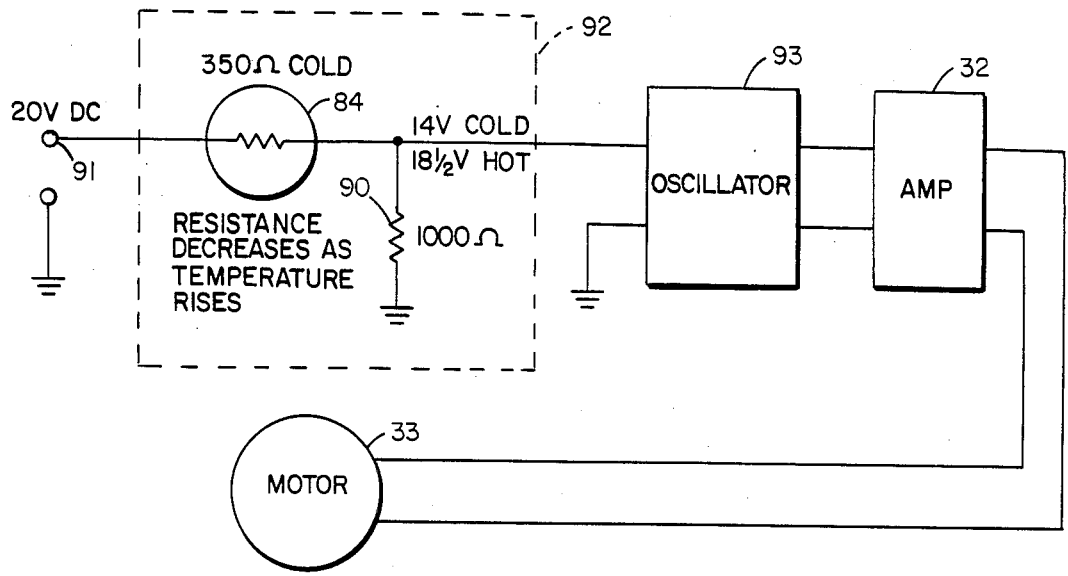
FIG. 2 is a diagrammatic illustration showing in more detail the temperature sensing and control aspect of the invention.

Circuit 40 can perhaps most easily be understood from a consideration of FIG. 2. In this figure resistor 90 which is in variable oscillator circuit 31 in FIG. 1 is separated out to clarify the description. Thermistor 84 is essentially a resistance element, the resistance of which decreases as temperature rises. Thermistor 84 is connected between the positive pole of a 20 volt DC source 91 and oscillator 93. (Oscillator 93 is variable oscillator circuit 31 minus resistor 90.) The line 89 between thermistor 84 and oscillator 93 is connected through a 1000 ohm resistor 90 to ground. This circuit 92 is essentially a voltage divider network which applies a voltage to oscillator circuit 93. This voltage is given by the equation $V_{osc} = R_x V/(R_t + R_x)$, where $V_{osc}$ is the voltage applied to the oscillator, $R_x$ is the fixed resistance 90, $R_t$ is the resistance of the thermistor 84 and V is the voltage of the DC source 91. This voltage is 14 volts when thermistor 84 is cold and gradually rises to approximately 18 ½ volts when thermistor 84 is at its maximum temperature (approximately 300° F.). This voltage is used to vary the power input to the oscillator which causes the oscillator output voltage to vary proportionally. The variance in the output voltage of oscillator 31 in turn causes the output voltage of amp 32 to vary in an amount just sufficient to offset the change in effective power produced by motor 33 which is caused by the resistance of the coils in the motor increasing with the rising temperature.

Referring back to FIG. 1, pressure sensing and control system comprises transducer 73 and a subcircuit within the meterboard 72A of meter 72, which will be discussed in detail below in connection with FIGS. 5A, 5E, 6 and 7. This system causes the lavage/irrigation amplifier 32 to turn off when the output signal from transducer 73 exceeds a predetermined level. In this manner the pressure in line 35 is caused to control motor 33 through the amplifier 32. In the preferred embodiment this control mechanism is utilized to provide a remote "pump switch." When pinch valve 17 is closed the pressure in line 35 will rise as motor 33 continues to pump. In prior art systems this condition was allowed to continue as long as valve 17 was held closed. In the present system however, transducer 73 reads the increased pressure signal from line 35 and its output increases above the predetermined level which the circuitry in meterboard 72A looks for. When this threshold level is reached or exceeded a circuit within meter 72 turns the input signal to amp 32 off. This turns off motor 33 and pump 34. Since while valve 17 is closed the fluid system comprising pump 34 line 35 and handpiece 10 is a closed system, the pressure in line 35 remains high until valve 17 is released, whereupon it decreases. As the pressure decreases the output of transducer 73 decreases and falls below the pre-determined level, whereupon the circuit within meter 72 turns the amplifier 32 on again, turning on motor 33 and pump 34, which resumes pumping at its previously set levels. Thus this pressure control system provides a remote "on" "off" switch to motor 33 with no apparent additional connections (from the viewpoint of the user) between the motor and the lavage handpiece 10. Thus, the invention enables the simplest handpieces of the prior art, which are both disposable and easily resterilizable, to be turned into remote control devices when incorporated with the present invention.

Figure 3:
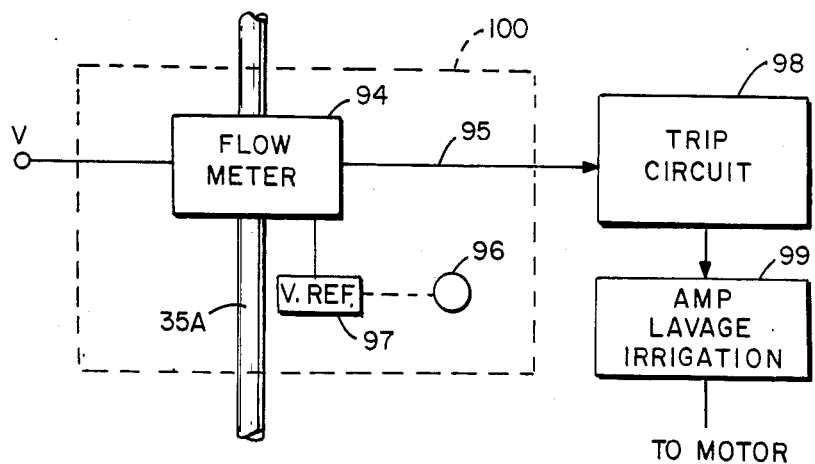
FIG. 3 is a diagrammatic view illustrating the rate of flow sensing and control aspect of the invention.

FIG. 3 shows an alternative embodiment of the invention which in some situations may be used as a replacement for the pressure control circuit 43 of FIG. 1. In this embodiment a flow meter 94 is placed in line 35A which corresponds to line 35 in the embodiment of FIG. 1. A back panel control 96 may be used to set a reference voltage for the flow meter in order that the voltage output of the flow meter on line 95 takes on an appropriate level to perform the required functions. When valve 17 is closed not only does the pressure in line 35 rise, but the flow goes to zero. This zero flow causes the output of flow meter 94 to decline to a predetermined reference level for example, zero voltage. This predetermined voltage level is detected by a trip circuit 98 which turns off the lavage irrigation amplifier 99. When switch 17 is opened the residual pressure within line 35 causes flow to take place, which flow is detected by flow meter 94, causing its voltage to rise above the predetermined level which in turn causes the trip circuit to turn on the amplifier 99 causing the system to resume operation. Similiarly the circuit in box 100 of FIG. 3 could be used to replace the circuit in box 92 of FIG. 2 in an alternative embodiment. These embodiments shall not be discussed in further detail; they are included herein to indicate variations that are possible within the inventive concept. The temperature and pressure embodiments discussed above and below have been found to work extremely well and thus are the preferred embodiments.

Figure 4A:
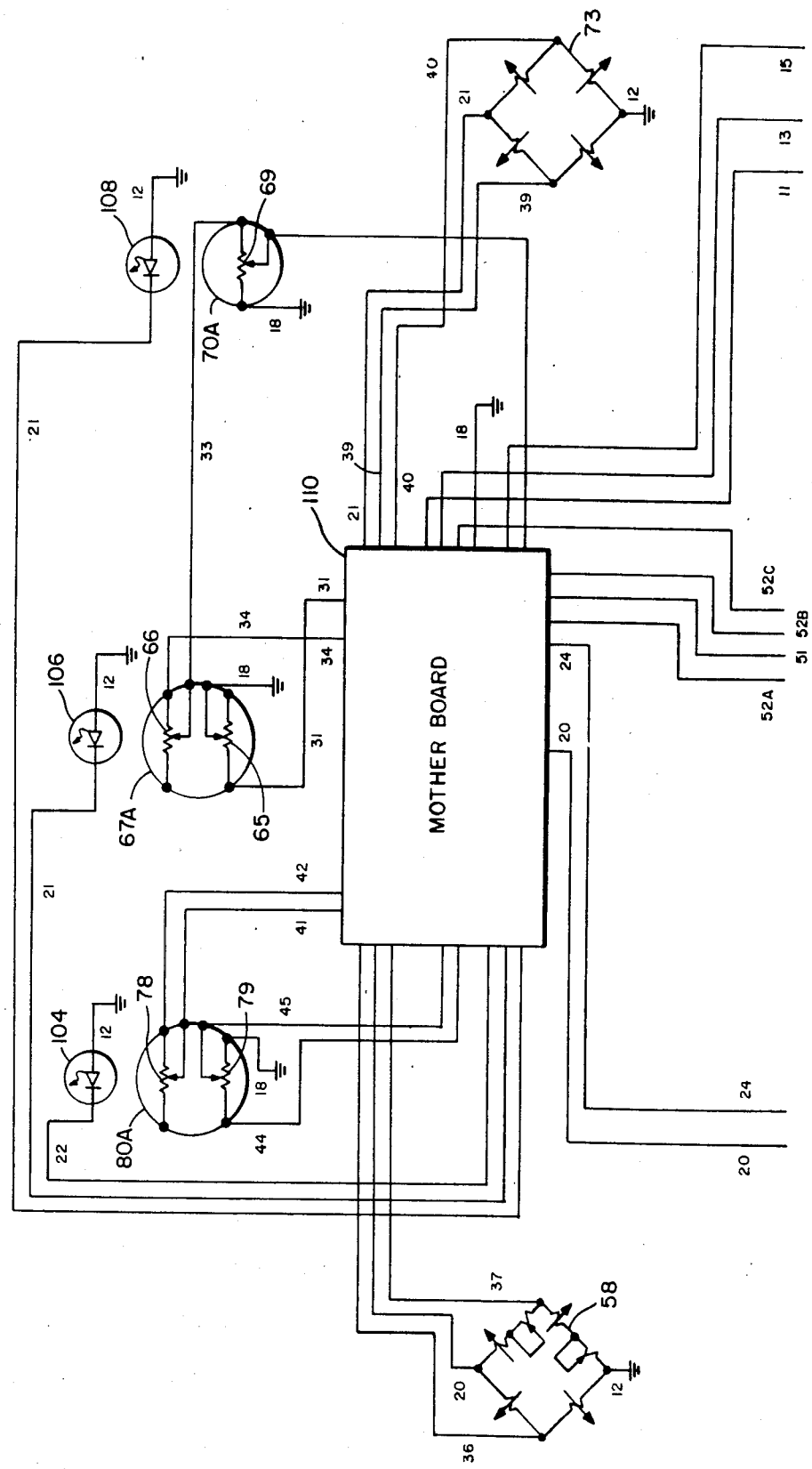
FIG. 4A is the upper half and FIG. 4B is the lower half of a schematic diagram of the electronics according to the preferred embodiment of the invention.
Figure 4B:
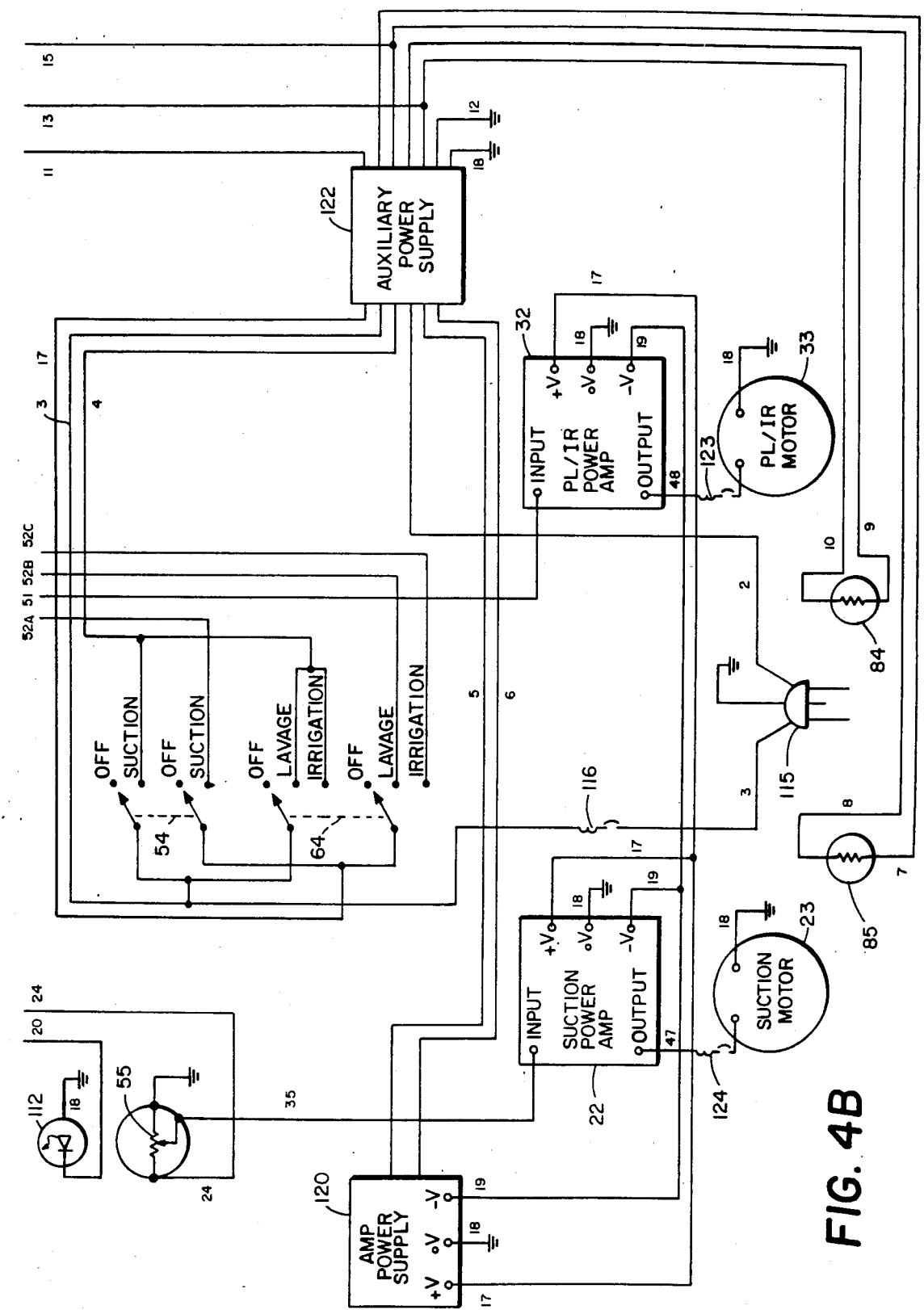

Turning now to a more detailed description of the electronic circuitry, the various electronic components and their electrical interconnection are shown in FIGS. 4A and 4B. If FIG. 4A is placed above FIG. 4B, so that the wires leaving FIG. 4A at the bottom of the page overlap the wires entering FIG. 4B at the top of the page, a complete electrical schematic of the electronic portion of the invention is obtained. The numbers contained in small circle in FIG. 4A and 4B label the individual wires, and thus enable the wires to be traced from one page of the drawing to the next. Note that some wires carry identical numbers, for example ㉑ and ⑱. This is an indication that these wires connect at some point, usually on the Motherboard 110. Beginning at the top of FIG. 4A and proceeding to the bottom of FIG. 4B, the components of the electrical circuit include light emitting diodes (LED) 104, 106, and 108 which are illuminated as appropriate to show that the irrigation function, the pulsatile lavage frequency control function, and the pulsatile lavage pressure control function respectively are operating. Beneath these diodes are two dual potentiometers 80A and 67A and a single potentiometer 70A which contain the variable resistors 78, 79, 65, 66, and 69. Variable resistors 66, 69 and 79 function as described above in connection with FIG. 1. Variable resistor 78 in dual pot 80A is part of the circuit regulating irrigation meter 81 to provide the proper meter output. Variable resistor 65 in dual pot 67A provides an adjustment to the gain of amplifier 32 to keep the amplifier output flat as the frequency changes. Potentiometers 80A, 67A, and 70A are controlled by knobs 80, 67, and 70 respectively (see FIG. 1). Beneath the dual pots are the irrigation/lavage transducer 73 and the suction transducer 58 also described in FIG. 1, and the Motherboard 110. Motherboard 110 is a hybrid circuit which provides for most of the connections between the various electrical components, which shall be described below in connection with FIGS. 5A through 5E. At the top left of FIG. 4B is suction LED 112 and the suction amplifier potentiometer 55 which functions as described in reference to FIG. 1. Switches 54 and 64 connect power socket 115 with the power supplies and the Motherboard 110 through circuit breaker 116. The amplifier power supply 120 supplies power to the amplifiers 22 and 32, while the auxiliary power supply 122 supplies power to the other components in the circuit. Amplifier 32 is connected to pulsatile lavage/ irrigation motor 33 through circuit breaker 123 while amplifier 22 is connected to suction motor 23 through circuit breaker 124 as discussed in reference to FIG. 1. The thermistors 84 and 85 which are mounted on motors 33 and 23 respectively, are connected with the auxiliary power supply 122 and the Motherboard 110 as indicated.

Figure 5A:
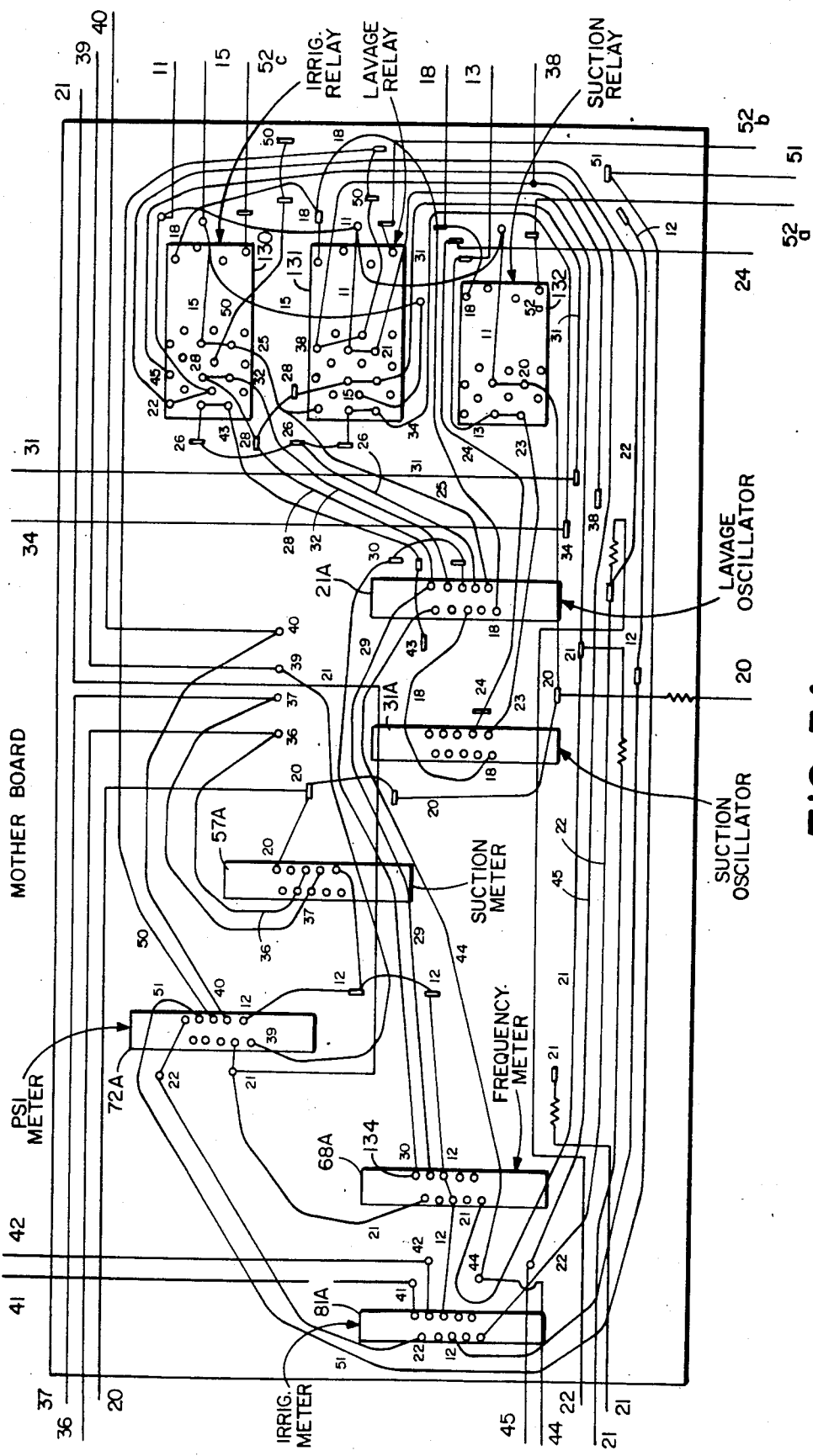
FIGS. 5A through 5E show a more detailed electrical schematic including the pressure sensing and control and temperature sensing and control aspects of the invention.
Figure 5B:
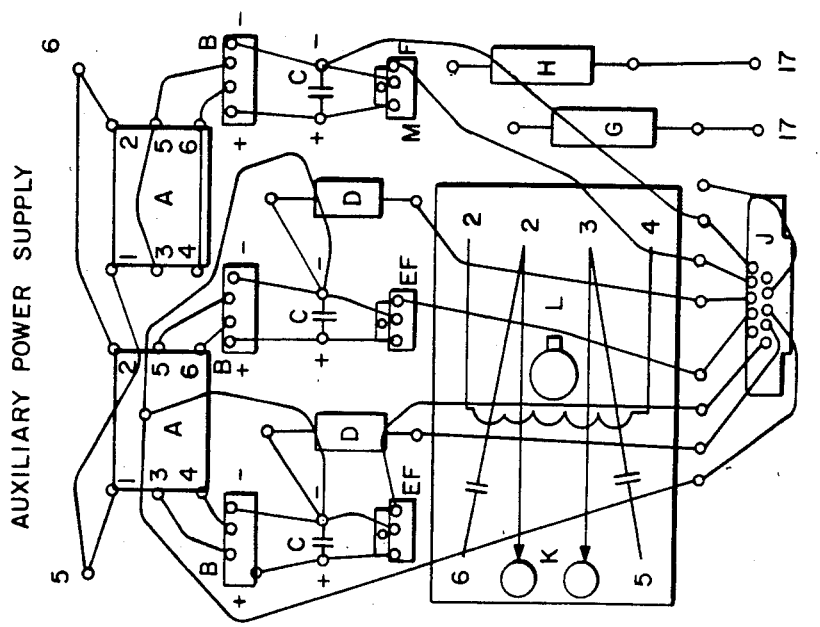
Figure 5C:
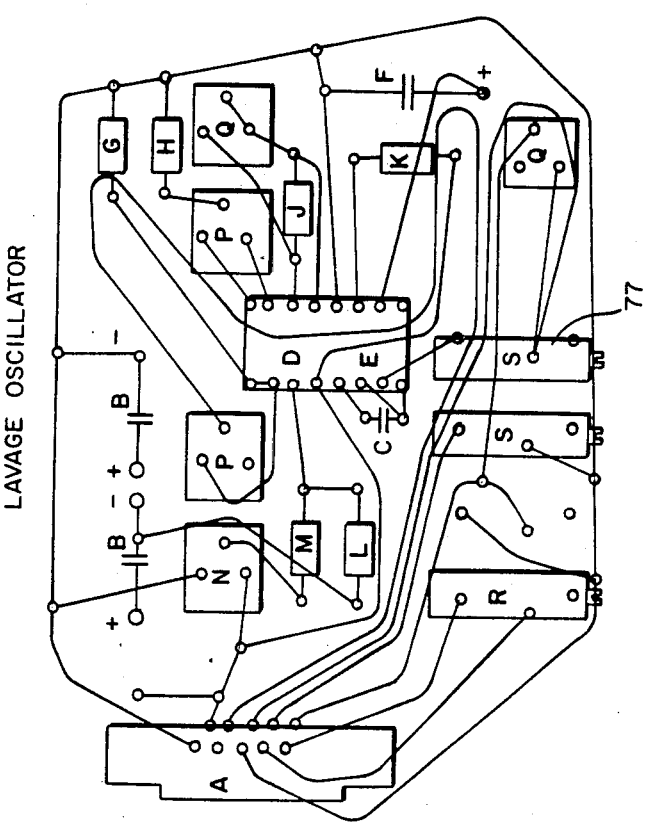
Figure 5D:
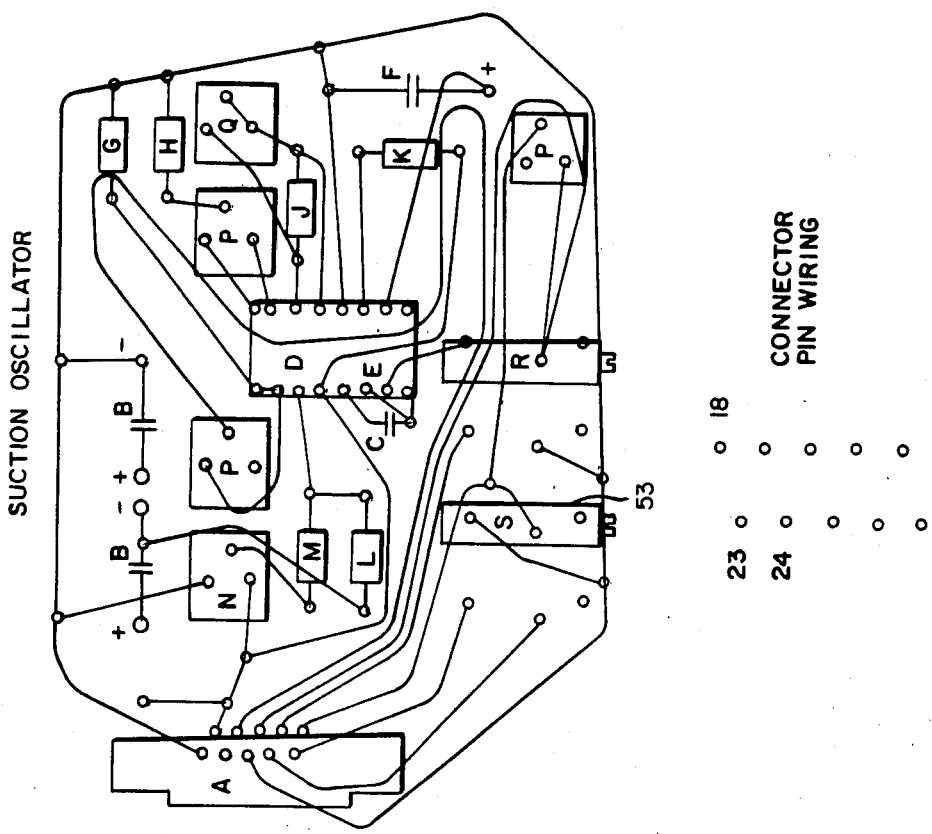

The Motherboard layout is shown in FIG. 5A. The Motherboard 110 includes six subsidiary boards: irrigation meter board 81A, frequency meter board 68A, PSI meter board 72A, suction meter board 57A, lavage oscillator board 31A, and suction oscillator board 21A. The details of the PSI meter board 72A, the lavage oscillator board 31A, and the suction oscillator board 21A are given in subsequent figures. The Motherboard 110 also includes three relays, the irrigation relay 130, the lavage relay 131, and the suction relay 132. The numbered wires shown coming into the Motherboard 110 from outside the figure are the numbered wires entering the Motherboard 110 in FIG. 4A and connecting to the various components shown in FIGS. 4A and 4B. Each of these connections can easily be traced from figure to figure using the numbered wires. The wires connecting the various components on the Motherboard 110 are also labeled with numbers within circles. These wires will be indicated on the detailed drawings of the component boards so that the interconnections will be clear. The ten heavy dots, such as 134, on each of the subsidiary boards are connector pins of WTB10PR7JTA connectors on each of the boards. The pin wiring to these connectors is shown in detail on the subquent figures. The connections between the subboards and the relays can easily be traced on the Motherboard 110 using the numbered wires, and thus they shall not be discussed further. Each of these amplifiers, meters, oscillators and transducers shown in FIGS. 10A, 10B, and 11A are devices that are well understood in the electrical art, which one skilled in the art can build once their function has been described. Instructions on the detailed connections, can usually be obtained with the purchase of the principal parts, and/or will generally be understood from the electrical literature. However, for completeness the detailed electrical components and connections between the components for the auxiliary power supply 122, the lavage/irrigation oscillator board 31A, the suction oscillator board 21A, and the PSI meter board 72A are shown in FIGS. 5B through 5E respectively. These are the boards that include the components primarily involved in the present invention. Each of the individual components is labeled and indicated on the drawings and each of the connections between the components are shown. In each of the drawings the circled numbers represent connections to wires coming into or located on the Motherboard 110. In each of the drawings which incorporates a WTB10PR7JTA connector, the wiring to the cable connector which presses into the WTB10PR7JTA connector is shown on the drawing. The wiring is shown as it would appear if one turned the cable connector so that the pins are visible and looked down at the pins, since this is the manner in which the cable connector is ordinarily viewed. In each of the drawings the position of the cable locator is shown by a star. The "behind the set" variable resistor 77 for setting the "fixed" irrigation frequency (see discussion of FIG. 1 above) is indicated on FIG. 5C, while the variable resistor 53 for setting the frequency of the fixed or suction oscillator 106 is indicated in FIG. 5D. It may be noticed that while the suction oscillator board (FIG. 5D) shows wires to nine sockets on the connector A, the connector pin wiring on the same figure shows connections to only three pins. This is due to the fact that the suction and lavage oscillator boards are wired the same for manufacturing convenience, but only three pins need be connected to the Motherboard 110 for the suction oscillator to operate properly.

Figure 5E:
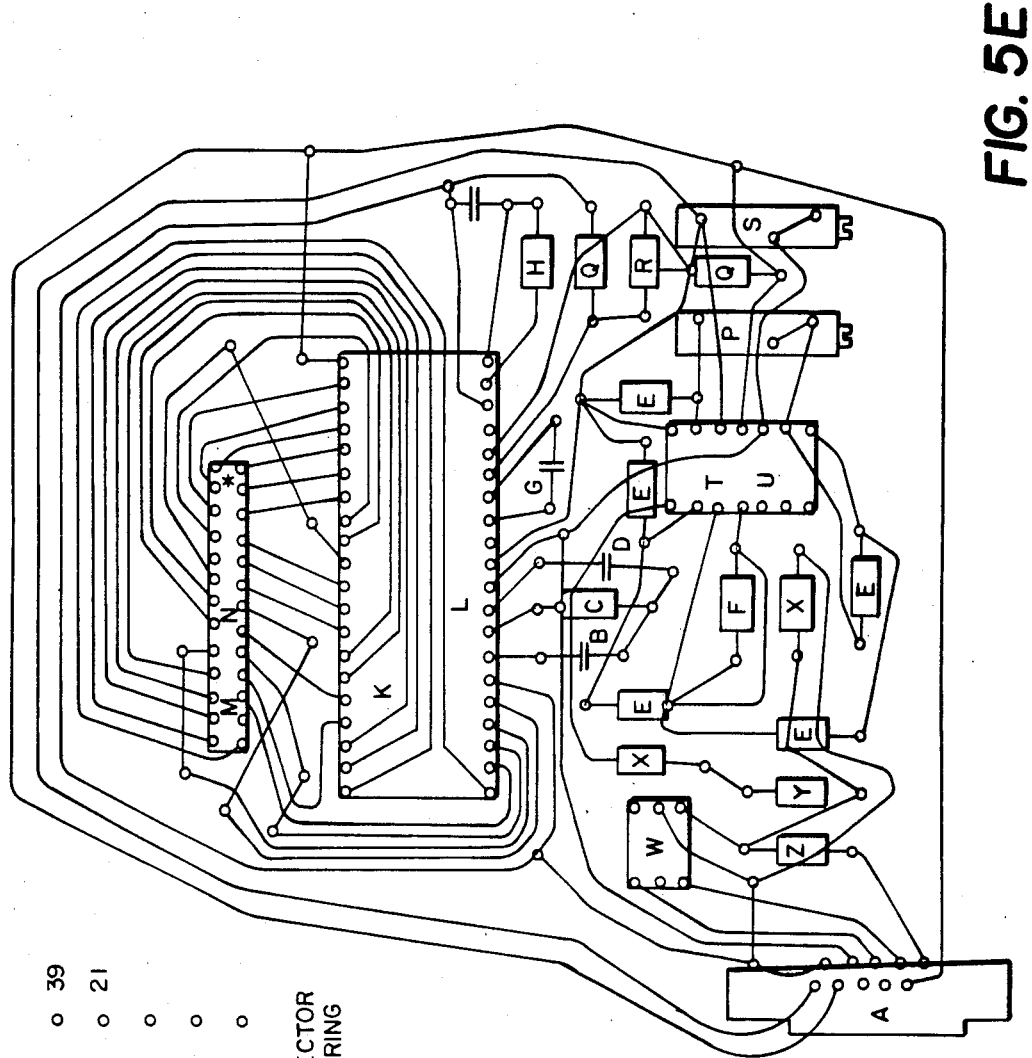
Figure 6:
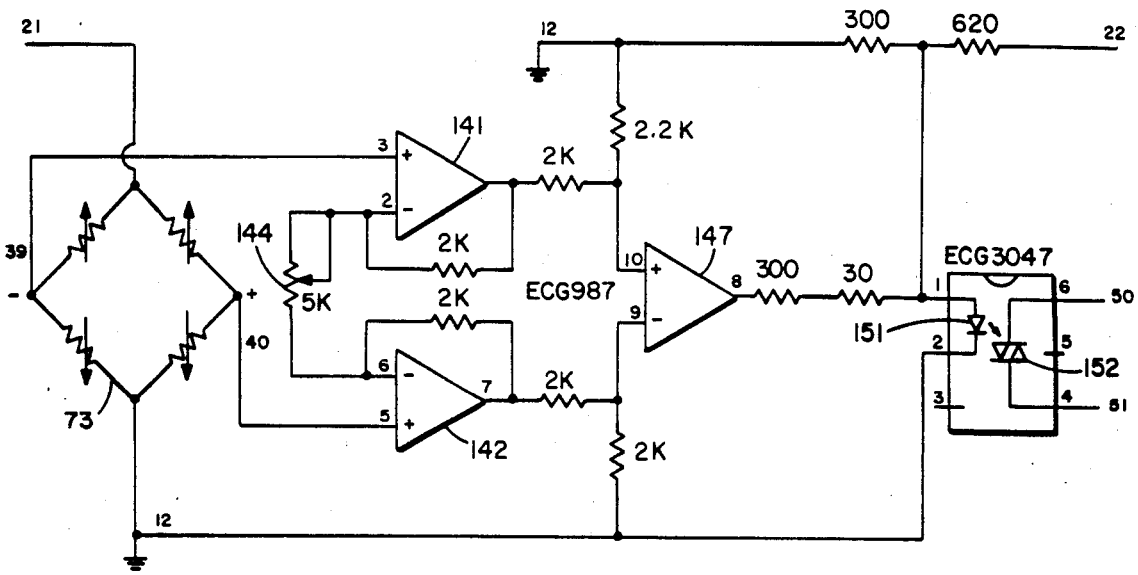
FIG. 6 is an electronic schematic of an embodiment of the pressure sensing and control circuitry.
Figure 7:
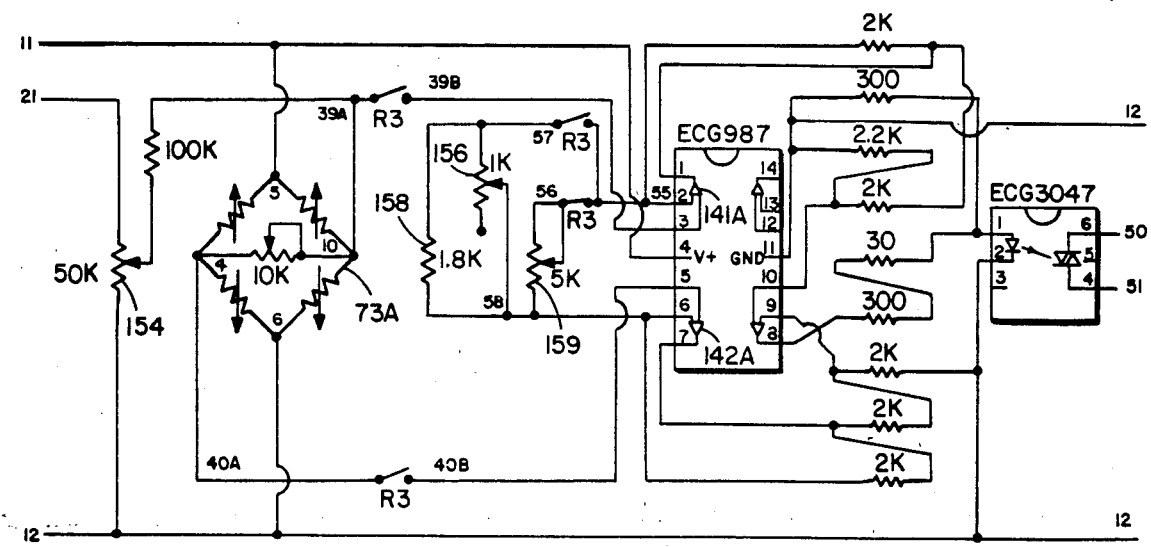
FIG. 7 is an electronic schematic of the preferred embodiment of the pressure sensing and control circuitry.

The details of the temperature sensing and control circuitry are shown in FIG. 2 and have already been discussed in connection with that figure. The pressure control circuit which is shown by the connection between transducer 73 and amplifier 32 thru meter 72 in FIG. 1 is located on the psi meter board (FIG. 5E) and consists of the ECG987 quad operational amplifier and the ECG3047 triac opto coupler. These are off-the-shelf items, and instructions for use of the items to produce appropriate circuits may be obtained with purchase of the items. The particular circuits used in two embodiments of the invention are shown in FIGS. 6 and 7. In these figures the circled numbers are line numbers as in previous figures, and the numbers on the terminals are the pin numbers of the ECG987 quad operational amplifier and the ECG3047 triac opto coupler as indicated.

FIG. 6 shows an embodiment in which the pressure at which the circuit turns the amplifier off is fixed; i.e., the trip point of the circuit is fixed. This circuit is the same embodiment as is shown in FIG. 4a and FIG. 5e; however, in FIG. 6 the various components of the two figures which relate to the pressure sensing and control circuit have been separated out and placed in juxtaposition so that their connection and function can be seen more easily. In this embodiment, two of the operational amplifiers, 141 and 142, are used as voltage amplifiers of nearly unity gain, to provide a small adjustment to the high and low voltage outputs from the pressure transducer 73, namely lines ㊵ and ㊴ respectively. The non-inverting input of op amp 141 is connected to the low output of transducer 73 while the non-inverting input of operational amplifier 142 is connected to the high output of transducer 73. Potentiometer 144 is connected across the inverting inputs of operational amplifiers 141 and 142. A 2K resistor is connected between the inverting input and the output of each of the operational amplifiers 141 and 142. The non-inverting input of operational amplifier 147 is connected to the output of operational amplifier 141 through a 2K resistor and is also connected to ground through a 2.2K resistor. The inverting input of operational amplifier 147 is connected to the output of operational amplifier 142 through a 2K resistance and also connected to ground through a 2K resistance. With these connections, potentiometer 144 may be used to adjust the relative values of the outputs of the op amps 141 and 142 and thus set the trip point of the system. Operational amplifier 147 acts as a comparator. Below the trip point the non-inverting input of op amp 147 will have a slightly higher voltage than the inverting input, and as the pressure increases the two voltages will approach one another. When the non-inverting input falls below the voltage of the inverting input operational amplifier 147 will turn off. The output of operational amplifier 147 is applied through a 330 ohm resistance and through gallium-arsenide infrared emitting diode 151 to ground. Thus when op amp 147 is on diode 151 will be on, and when op amp 147 is off, diode 151 will be off also. While diode 151 is on a silicon bilateral switch 152 senses the radiation and turns on connecting lines 50 and 51. Line 50 is the output from the oscillator 31 while line 51 is the input to lavage/irrigation amplifier 32. Thus if the pressure is below the trip point the circuit of FIG. 6 will permit the signal from oscillator 31 to pass to amplifier 32, while at pressures above the trip point diode 151 turns off causing switch 152 to open preventing the signal from oscillator 31 from reaching amplifier 32, and thus turning off the motor 33.

FIG. 7 shows an embodiment of the pressure sensing and control circuitry in which the trip point is variable in the pulsatile lavage mode. This embodiment is presently the preferred embodiment. This circuit is the same as the circuit of FIG. 6 with the following differences. The voltage of the low terminal of pressure transducer 73A is adjustable by means of potentiometer 154. An additional potentiometer 156 and an additional 1.8K resistance 158 are connected across the inverting inputs of operational amplifiers 141A and 142A. In this embodiment the setting of potentiometer 156 is controlled by the pressure control knob; that is, the potentiometer 70A of the embodiment of FIG. 4a is replaced by a dual potentiometer, with the second potentiometer of the dual pair being potentiometer 156. Resistance 158 is preferrably chosen so that the trip point of the circuit stays about 10 psi above the pressure setting selected by the control knob. Potentiometer 159 is used to set the trip point for the system when it is in irrigation mode; the irrigation mode trip point is a "fixed" trip point in that it does not vary with the pressure control, and the circuitry for setting this "fixed" trip point is identical to the circuitry of FIG. 6, with potentiometer 159 playing an analogous role to potentiometer 144 of FIG. 6. The switches indicated by R3 in FIG. 7 are tripped by the irrigation relay when the system is switched between the pulsatile lavage mode and the irrigation mode, in order to switch control of the trip point setting between the circuit of potentiometer 156 and the circuit of potentiometer 159.

Most of the electrical parts to produce the circuits described above are common parts, the identity of which unambiguously disclosed by the labels on the figures. The flow meter utilized in the embodiment of FIG. 3 may be any one of a variety of flow meters available, for example, a model 100 flow switch available from Proteus Industries, Inc., 240 Polaris Ave., Mountain View Calif. 94043. The connectors such as the WTB10PR7JTA are made by Airborn, Inc. of Addison, Tx. 75001. The Stancor PPC-3 power transformer may be purchased from Newark Electronics at 1225 North Main, North Canton, OH. The suction power amp is an English amplifier designated ILP Y-200 and may be purchased from Gladstone Electronics, 901 Fuhrman Blvd., Buffalo, N.Y. The suction transducer is a Foxboro 1800 transducer: it and the balance resistors which form part of the transducer 58 and are shown in FIG. 4A may be obtained from Foxboro/ICT at 1750 Junction Ave., San Jose, Calif. The pulsatile lavage/irrigation transducers 73 and 73A are off-the-shelf Foxboro 703 transducers. The suction and pulsatile lavage/irrigation thermistors 84 and 85 are Oneida GB1224 thermistors and may be purchased from Oneida at Box 678 Road 2, Baldwin Extension, Meadville, Pa. 16335. All other parts may be purchased from an electronics distributor, such as Canico, Inc. 1355 Shoreway Rd., Belmont, Calif. 94002.

It is a feature of the invention that the control of pulsatile lavage/irrigation pump 34 by pinch valve 17 which the invention provides, not only allows for remote control of the pump motor 33 at the lavage site, but also is highly efficient when compared to the prior art devices. The remote control prevents laboring of the pulsatile/irrigation pump 34 when valve 17 is closed, which adds significantly to the longevity of the system, and significantly reduces the noise of the system. In particular, the fan noise which was always present with previous systems is eliminated because the efficiency permits the fan to be eliminated. The invention also significantly reduces the risk of bursting pressure lines, as well as the risk of sudden flows of fluid when they are not desired.

It is another feature of the invention that the elimination of the erratic pressures and flow rates permits a much broader use of a lavage system under desirable medical conditions. For example, the lavage system of the invention may be utilized on a written prescription basis, for example, in a post-operative stage when the actual care is to be administrered by nurses or other paramedical personnel, which was usually not contemplated with prior art instruments because of their idiosyncracies. It is anticipated that other uses may be found by physicians as they learn about the controllability and ease of use of the system of the invention.

A novel lavage system that provides improved control and stability over a broad range of pulsatile lavage, irrigation, and aspiration functions, and has numerous other features and advantages has been described. While the above description of the invention has been referenced to a few particular embodiments, it is evident that, now that the advantages of using the operating conditions of the system for control of a lavage system have been disclosed, those skilled in the art can now make numerous usues of, modifications of, and departures from the specific embodiments described herein without departing from the inventive concepts. For example, the system could be simplified to provide only one of any of the three lavage functions (pulsatile lavage, irrigation, and aspiration), or it may be expanded to include a pulsatile aspiration function, in addition to the other functions, or any combinations of functions. Likewise, other operating conditions or combinations of operating conditions may be used in any one of such systems, so long as the claimed features are included. Or for example, the output of the thermistor circuit 92 may be applied to control the amplifier 32 directly rather than through the oscillator. It is clear that now that the principles of invention have been disclosed, much of the system may be replaced by equivalent parts; as for example as wide variety of equivalent electronic parts are available that will provide the inventive functions. Consequently the invention is to be construed as embracing each and every novel feature and novel combination features within the appendid claims.

What I claim is:

1. A lavage system comprising:
   a means for producing a pulsatile fluid flow including a motor and means for furnishing a power signal to said motor:
   a means for sensing a temperature condition of said motor and for providing a signal respresentative of said condition;
   a means responsive to said condition signal for controlling said means for producing in a predetermined manner to effect a change in said power signal; and
   said means for sensing includes a means for sensing a fluid pressure within the lavage system, said means for controlling comprises a means for turning said means for producing a pulsatile fluid flow off when said pressure exceeds a predetermined value and for turning the means for producing a pulsatile fluid flow on when the pressure equals or falls below said value and further including means for adjusting said pressure and said predetermined value.

2. A lavage system comprising:
   a means for producing a pulsatile fluid flow including a motor and means for furnishing a power signal to said motor:
   a means for sensing a temperature condition of said motor and for providing a signal representative of said condition; and
   a means responsive to said condition signal for controlling said means for producing in a predetermined manner to effect a change in said power signal, said means for sensing is also responsive to the rate of flow of fluid in at least a portion of said system.

* * * * *